United States Patent
Mansell

(10) Patent No.: US 11,331,399 B2
(45) Date of Patent: May 17, 2022

(54) STERILIZING SURGICAL INSTRUMENT TABLE

(71) Applicant: John Mansell, Gillette, WY (US)

(72) Inventor: John Mansell, Gillette, WY (US)

( * ) Notice: Subject to any disclaimer, the term of this patent is extended or adjusted under 35 U.S.C. 154(b) by 0 days.

(21) Appl. No.: 16/647,819

(22) PCT Filed: Sep. 20, 2018

(86) PCT No.: PCT/US2018/052054
§ 371 (c)(1),
(2) Date: Mar. 16, 2020

(87) PCT Pub. No.: WO2019/060617
PCT Pub. Date: Mar. 28, 2019

(65) Prior Publication Data
US 2020/0215212 A1  Jul. 9, 2020

Related U.S. Application Data

(60) Provisional application No. 62/562,036, filed on Sep. 22, 2017.

(51) Int. Cl.
*A61L 2/10* (2006.01)
*A61B 50/15* (2016.01)

(52) U.S. Cl.
CPC .............. *A61L 2/10* (2013.01); *A61B 50/15* (2016.02); *A61L 2202/16* (2013.01); *A61L 2202/24* (2013.01)

(58) Field of Classification Search
CPC .... A61L 2/10; A61L 2202/16; A61L 2202/24; A61B 50/13; A61B 50/15; A61B 50/24
See application file for complete search history.

(56) References Cited

U.S. PATENT DOCUMENTS

| | | | |
|---|---|---|---|
| 8,074,815 B2 * | 12/2011 | Gerstner | A61B 50/20 211/193 |
| 2002/0085947 A1 | 7/2002 | Deal | |
| 2003/0034459 A1 * | 2/2003 | Bonin | A61L 2/06 250/491.1 |
| 2007/0023710 A1 * | 2/2007 | Tom | A61L 2/24 250/504 R |

(Continued)

FOREIGN PATENT DOCUMENTS

| | | |
|---|---|---|
| EP | 1905343 A1 | 4/2008 |
| KR | 1020130131958 A | 12/2013 |
| KR | 1020170022190 A | 3/2017 |

OTHER PUBLICATIONS

Korean Patent Office, International Search Report issued in corresponding application PCT/US2018/052054; dated Apr. 8, 2019, 4 pages.

(Continued)

*Primary Examiner* — Wyatt A Stoffa
(74) *Attorney, Agent, or Firm* — Barnes & Thornburg LLP; Jerry C. Harris, Jr.

(57) ABSTRACT

Embodiments of the disclosure include an uncovered ultraviolet light emitting panel for use in supporting instruments in an operating room. The panel fits inside an autoclave for sterilization and can be utilized without a sterile cover. In use, the panel irradiates surgical instruments and the nearby air continuously.

6 Claims, 9 Drawing Sheets

(56) References Cited

U.S. PATENT DOCUMENTS

| | | | | |
|---|---|---|---|---|
| 2008/0265179 | A1* | 10/2008 | Havens | A61L 2/10 |
| | | | | 250/492.1 |
| 2009/0045154 | A1* | 2/2009 | Gerstner | A61B 50/33 |
| | | | | 211/126.15 |
| 2009/0275254 | A1* | 11/2009 | Green | G02B 6/0036 |
| | | | | 445/24 |
| 2011/0243789 | A1* | 10/2011 | Roberts | A61L 2/10 |
| | | | | 422/24 |
| 2012/0328474 | A1* | 12/2012 | Campagna | A61L 2/10 |
| | | | | 422/23 |
| 2013/0259742 | A1* | 10/2013 | Kerr | A61L 2/10 |
| | | | | 422/24 |
| 2015/0069265 | A1* | 3/2015 | Smetona | H05B 45/10 |
| | | | | 250/455.11 |
| 2015/0367008 | A1* | 12/2015 | Romo | A61L 9/20 |
| | | | | 422/24 |
| 2016/0114067 | A1* | 4/2016 | Dobrinsky | G01N 21/6486 |
| | | | | 250/461.1 |
| 2017/0027347 | A1* | 2/2017 | Kovacs | A47G 23/06 |
| 2017/0197002 | A1* | 7/2017 | Dobrinsky | A61L 2/10 |
| 2017/0216468 | A1 | 8/2017 | Romo et al. | |
| 2018/0104368 | A1* | 4/2018 | Dobrinsky | A61L 2/10 |
| 2019/0336632 | A1* | 11/2019 | Dombrowsky | H05B 47/11 |
| 2019/0351082 | A1* | 11/2019 | Martz | A61L 2/085 |
| 2020/0009279 | A1* | 1/2020 | Janssen | B01D 53/72 |
| 2020/0405899 | A1* | 12/2020 | Yang | A61L 2/10 |
| 2021/0007510 | A1* | 1/2021 | Gundry | F21V 7/04 |
| 2021/0113723 | A1* | 4/2021 | Malinowski | A47G 23/0216 |

OTHER PUBLICATIONS

Korean Patent Office, Written Opinion issued in corresponding application PCT/US2018/052054; dated Apr. 8, 2019, 8 pages.

Korean Patent Office, International Preliminary Report on Patentability issued in corresponding application PCT/US2018/052054; dated Mar. 4, 2020, 9 pages.

European Patent Office, Supplemental Search Report issued in corresponding application EP18859558.1; dated May 12, 2021, 7 pages.

* cited by examiner

US 11,331,399 B2

STERILIZING SURGICAL INSTRUMENT TABLE

CROSS-REFERENCE TO RELATED APPLICATIONS

This application is a filing under 35 U.S.C. 371 of International Application No. PCT/US2018/052054 filed Sep. 20, 2018, which is continuation of and claims priority to U.S. Provisional Patent Application Ser. No. 62/562,036, filed Sep. 22, 2017, by John Mansell and entitled "Sterilizing Surgical Instrument Table" which is incorporated herein by reference as if reproduced in its entirety.

FIELD OF THE INVENTION

The present invention is related to tables and surfaces that support and protect instruments used during surgical procedures.

BACKGROUND

Typical instrument tables found in medical operating rooms are fitted with sterile covers, and used as a staging area for medical instruments used in surgeries. Surgical infections are nonetheless still a serious problem. Bacteria migrate using air currents (e.g., Brownian motion or microcurrents due to motion in the room) and dust. Thus, air movement, noise level, and length of the operation all influence the likelihood of infections due to surgery. A need exists to reduce the pro-infection effects of correlation of air movement and other factors on infection rates.

SUMMARY

An uncovered ultraviolet light emitting panel is disclosed for use in supporting instruments in an operating room. The panel fits inside an autoclave for sterilization and therefore can be utilized without a sterile cover. In use, the panel irradiates surgical instruments and the nearby air continuously.

In an embodiment, an apparatus may comprise a first plurality of ultraviolet light emitting diodes positioned on a first substrate; a first sheet of transparent material in thermal contact with the first plurality of ultraviolet light emitting diodes; a first frame surrounding the first substrate and the first sheet, forming a first panel; and a mobile platform to support the first panel over a floor, the mobile platform adapted to receive the first panel in a configuration such that light emitted from the first plurality of ultraviolet light emitting diodes is directed in an upward direction from the floor.

In an embodiment, an assembly method may comprise positioning a first plurality of ultraviolet light emitting diodes on a first substrate; fixing a first sheet of transparent material in thermal contact with the first plurality of ultraviolet light emitting diodes; forming a first frame surrounding the first substrate and the first sheet, forming a first panel; and assembling a mobile platform to support the first panel over a floor, the mobile platform adapted to receive the first panel in a configuration such that light emitted from the first plurality of ultraviolet light emitting diodes is directed in an upward direction from the floor.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

"LED" herein refers to a light emitting diode which may comprise a semiconductor diode that glows when a voltage is applied.

"UV" herein refers to ultraviolet light, e.g., electromagnetic radiation having a wavelength shorter than that of the violet end of the visible spectrum but longer than that of X-rays and/or equipment or techniques using or concerned with such radiation.

"UV LED" and/or "ultraviolet LED" herein refer to an ultraviolet light emitting diode, i.e., a light emitting diode capable of transmitting and/or producing ultraviolet light.

"Release mechanism" herein refers to a latch, friction coupling, threaded device, etc. which can be operated by hand without tools to quickly (e.g., within 2-10 seconds) disengage a UV panel from the underlying bracket or table top supporting it.

Figure 1:
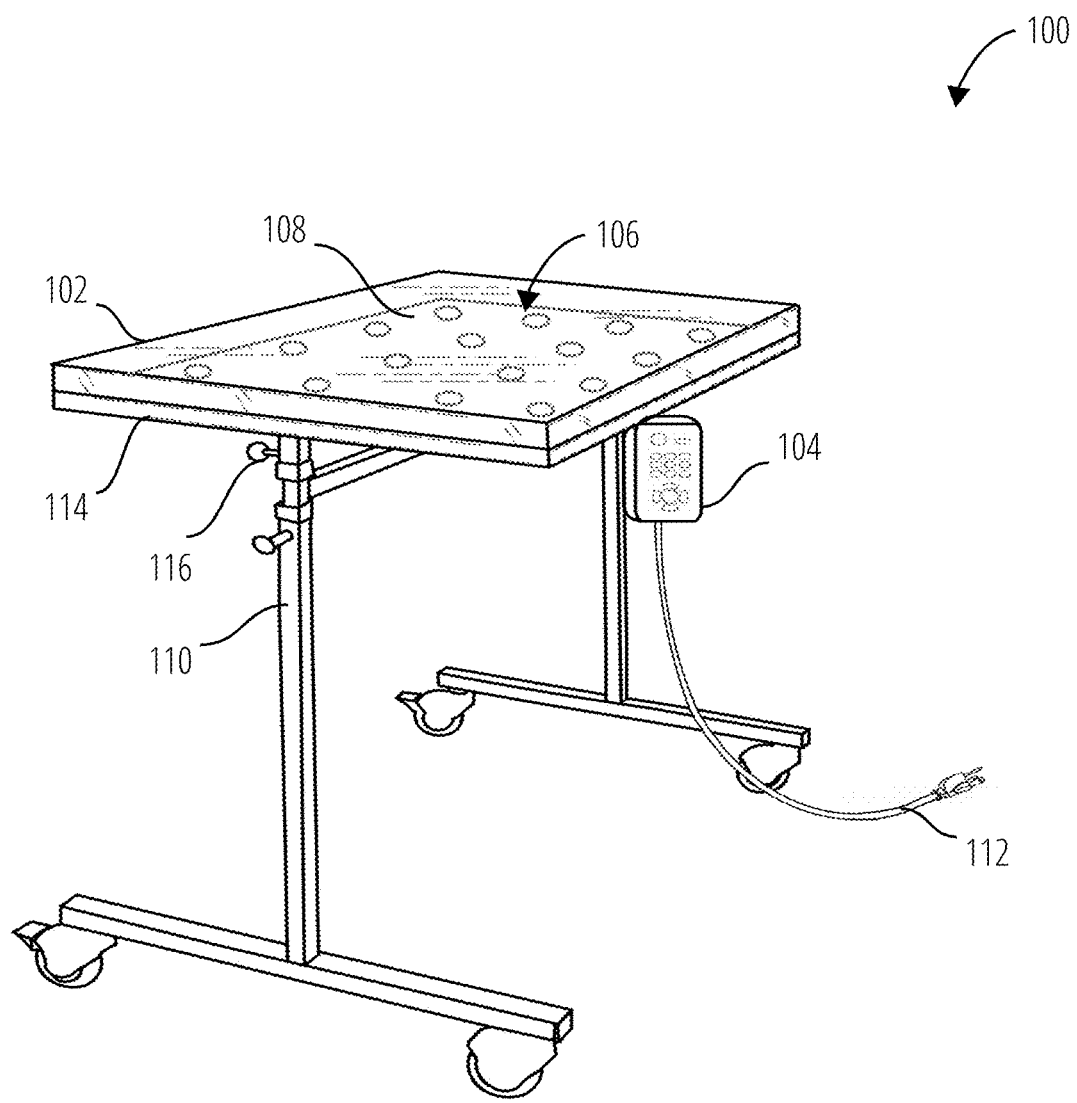
FIG. 1 illustrates a sterilizing instrument table 100 in accordance with one embodiment.

FIG. 1 illustrates a sterilizing instrument table 100 in accordance with one embodiment. The sterilizing instrument table 100 may comprise a sterilizing panel 102 supported by a stand 110, and a controller 104 connected to the sterilizing panel 102 and configured to control the operation of the sterilizing panel 102. The sterilizing panel 102 and controller 104 may be powered via a power cable 112.

The sterilizing panel 102 may include an LED array 106, which may be mounted on a panel substrate 114, and a transparent cover 108 which may fit over the LED array 106. The LED array 106 may comprise one or more ultraviolet light emitting diodes (UV LEDs). In some embodiments, one or more elements of the sterilizing instrument table 100 may be controlled and/or adjusted by operation of the associated release mechanism 116. The release mechanism 116 may be configured to move one or more spring-loaded table base attachments (which may be incorporated into and/or part of the stand 110), where the spring-loaded table base attachments may comprise notched bayonet fixator and/or locking parts, to allow for removal of the panel substrate 114 (which may comprise and/or be attached to a table top, as described in more detail below).

Figure 3:
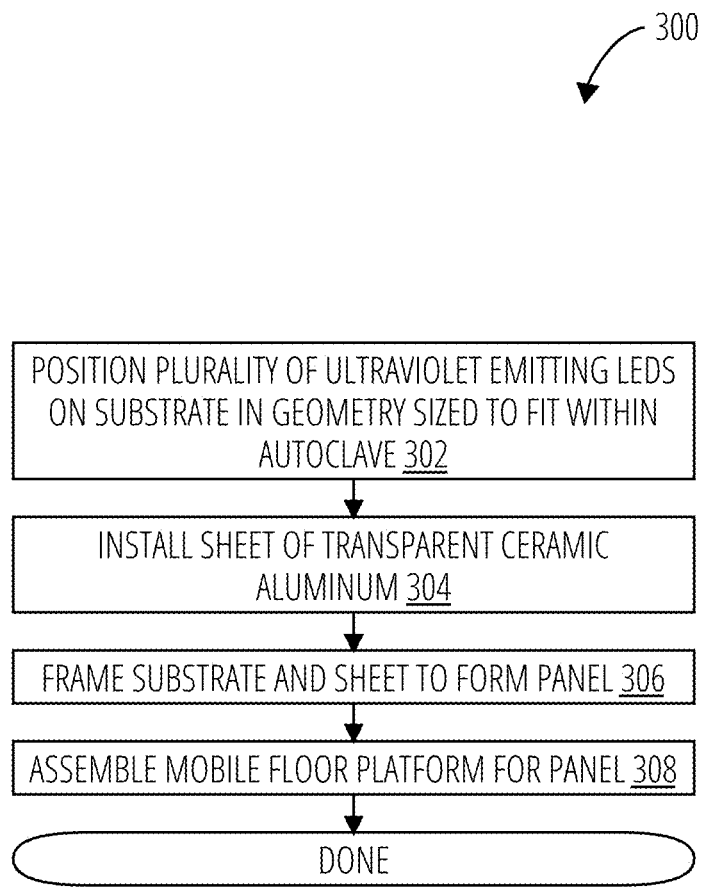
FIG. 3 illustrates an assembly process 300 in accordance with one embodiment.

An embodiment of the sterilizing instrument table 100 may be constructed according to the assembly process 300 of FIG. 3.

Figure 2:
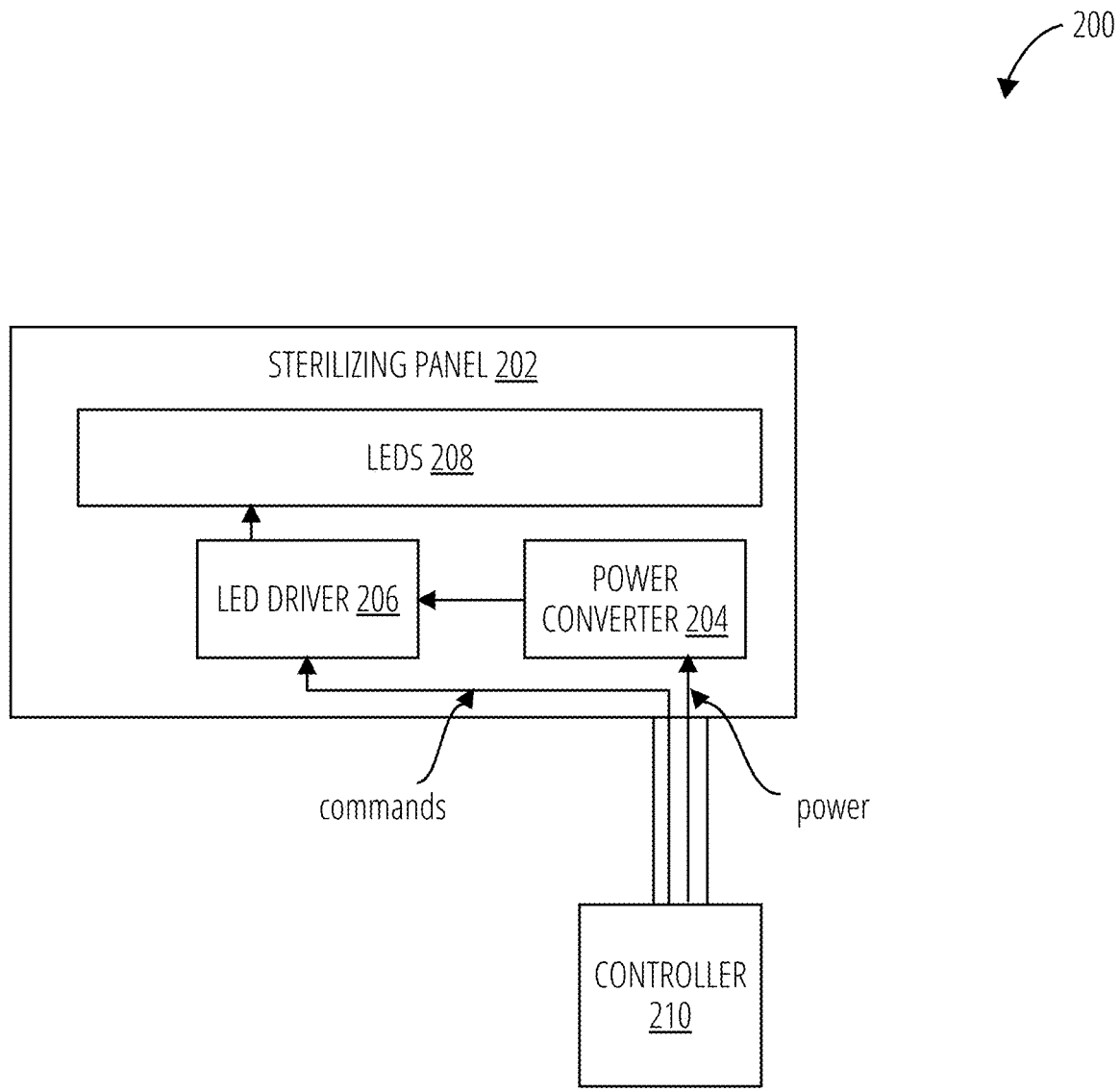
FIG. 2 illustrates a sterilizing panel system 200 in accordance with one embodiment.

FIG. 2 illustrates a sterilizing panel system 200 in accordance with one embodiment. The sterilizing panel system 200 comprises a sterilizing panel 202, a power converter 204, an LED driver 206, LEDs 208, and a controller 210. The controller 210 provides electrical power to the power converter 204, which converts the electrical power to form suitable to the LED driver 206. The controller 210 further provides commands to the LED driver 206, the commands generated by operation of a user interface of the controller 210. The LED driver 206 powers and/or controls the output of the LEDs 208, or subsets thereof, according to the commands from the controller 210.

FIG. 3 illustrates an assembly process 300 in accordance with one embodiment. In block 302, a plurality of ultraviolet LEDs are positioned on a substrate in a geometry sized to fit within an autoclave. In block 304, a sheet of transparent ceramic aluminum (or other UV transparent sterilizable material) is installed in thermal contact with at least a portion of the LEDs, eliminating any air gap between the LEDs and the sheet. Although this seems counterintuitive, an unforeseen benefit may be that, during exposure to extremes of heat such as during the sterilizing process, expansion and contraction of the transparent ceramic aluminum due to cycling air between the substrate and transparent ceramic aluminum is mitigated (such air cycling may induce fractures and eventually cause fatigue cracking of the transparent ceramic aluminum). In block 306, the substrate and sheet are framed to form a panel. In block 308, a mobile floor platform is assembled for the panel.

Figure 4:
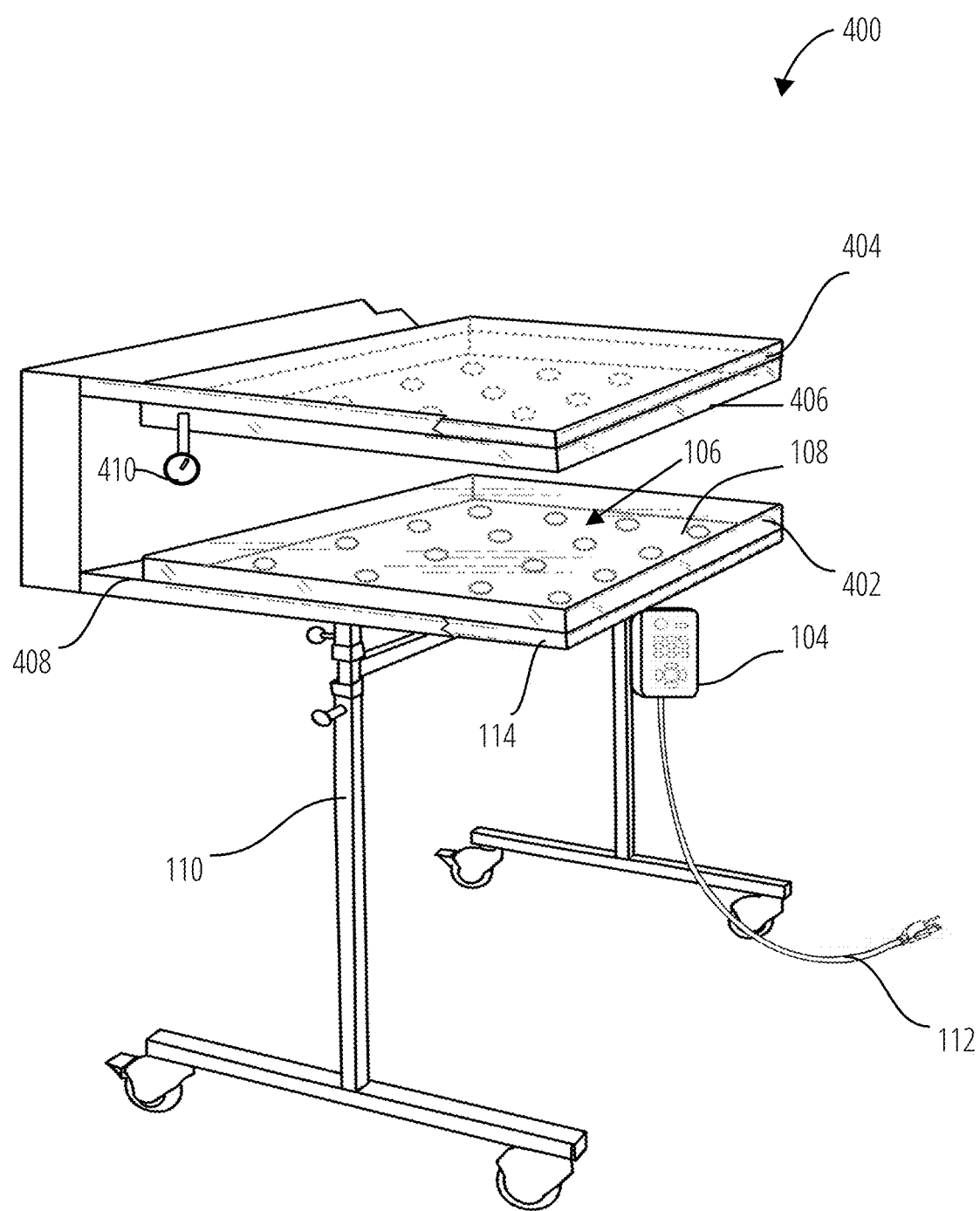
FIG. 4 illustrates a sterilizing instrument table 400 in accordance with another embodiment.

FIG. 4 illustrates a sterilizing instrument table 400 in accordance with another embodiment. The sterilizing instrument table 400 includes a lower sterilizing panel 402 (comprising a first LED array 106 comprising a plurality of UV LEDs) and an upper sterilizing panel 404 (comprising a second LED array 107 comprising a plurality of UV LEDs) assembled such that the transparent cover 108 of the lower sterilizing panel 402 and the transparent cover 406 of the upper sterilizing panel 404 are facing one another. Thus, sterilizing radiation from the upper sterilizing panel 404 is directed toward the lower sterilizing panel 402, and vice versa.

The lower sterilizing panel 402 and the upper sterilizing panel 404 are maintained in their relative configuration by a mounting frame 408. The mounting frame 408 is formed so that no edges, brackets, or flanges protrude onto or above the transparent (sterilizing) surfaces of the panels. At least the lower sterilizing panel 402 is removable from the mounting frame 408 for processing in (for example) an autoclave. The sterilizing instrument table 400 may comprise an air flow or sound sensor 410, which may provide signals to the controller 104 which then operates logic to adjust the intensity of light emitted from the first LED array 106 and/or the second LED array 107 in response to changes in air flow and/or air agitation. An embodiment of the sterilizing instrument table 400 may be constructed according to the assembly process 500 of FIG. 5.

Figure 5:
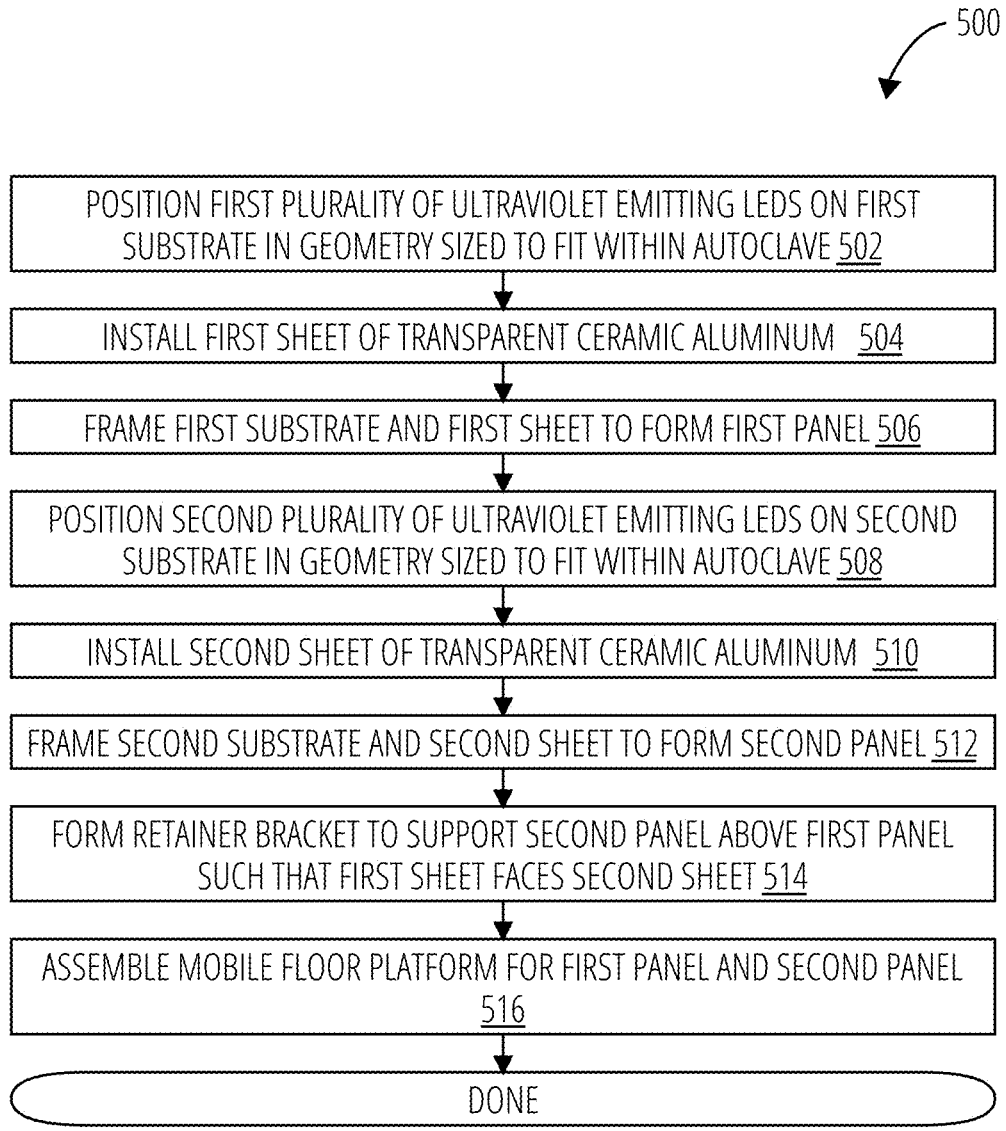
FIG. 5 illustrates an assembly process 500 in accordance with one embodiment.

Referring to FIG. 5, in block 502, a first plurality of ultraviolet LEDs are positioned on a first substrate in a geometry sized to fit within an autoclave. In block 504, a first sheet of transparent ceramic aluminum (or other UV transparent sterilizable material) is installed in thermal contact with at least a portion of the first LEDs. In block 506, the first substrate and first sheet are framed to form a first panel. In block 508, a second plurality of ultraviolet LEDs are positioned on a second substrate in a geometry sized to fit within the autoclave. In block 510, a second sheet of transparent ceramic aluminum (or other UV transparent sterilizable material) is installed in thermal contact with at least a portion of the second LEDs. In block 512, the second substrate and second sheet are framed to form a second panel. In block 514, a retainer bracket is formed to support the second panel above the first panel such that the first sheet faces the second sheet. In block 516, a mobile floor platform is assembled for the first panel.

Figure 6A:
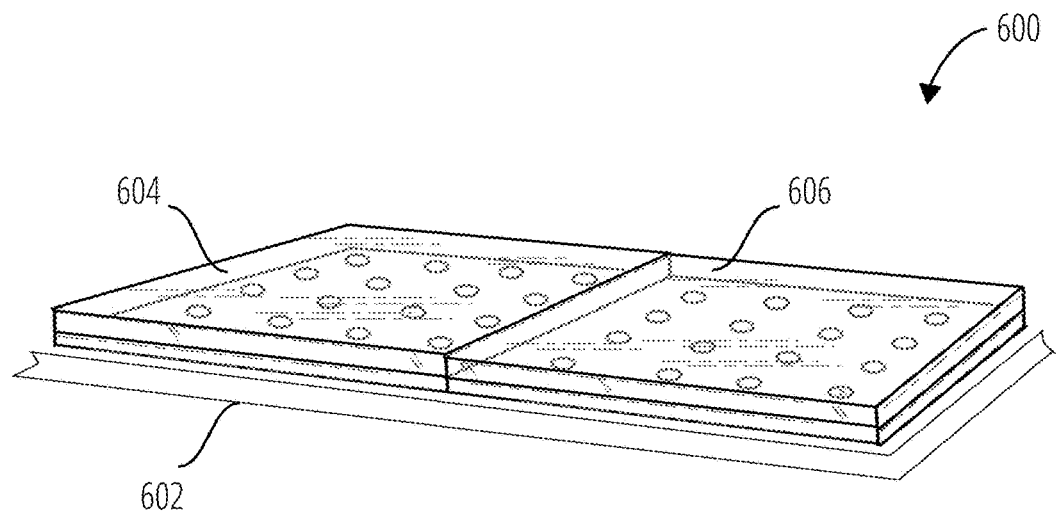
FIGS. 6A-6C illustrate a sterilizing instrument table 600 in accordance with yet another embodiment.
Figure 6B:
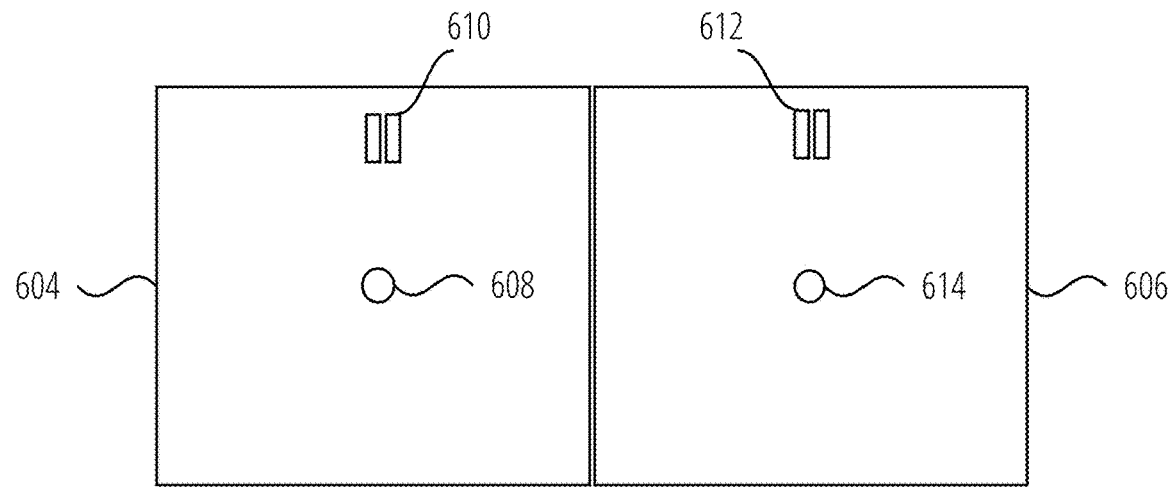
Figure 6C:
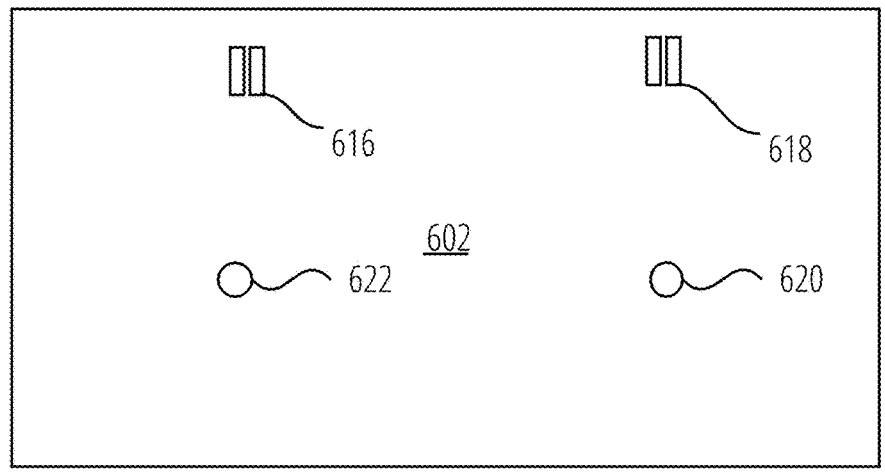

FIGS. 6A-6C illustrate a sterilizing instrument table 600 in accordance with yet another embodiment. The sterilizing instrument table 600 comprises a table top 602, a first sterilizing panel 604, and a second sterilizing panel 606.

As shown in FIG. 6B, the first sterilizing panel 604 includes a retention plug 608 and a power port 610, and the second sterilizing panel 606 includes a retention plug 614 and a power port 612.

As shown in FIG. 6C, the table top 602 includes a power port 616 and a power port 618, and a retention plug 620 and retention plug 622. The first sterilizing panel 604 and the second sterilizing panel 606 may be independently installed and removed from the table top 602. The first sterilizing panel 604 is powered by engaging the power port 610 with the power port 616, and the second sterilizing panel 606 is powered by engaging the power port 612 with the power port 618. The retention plug 608 engages the retention plug 622 to secure the first sterilizing panel 604 to the table top 602; likewise, the retention plug 614 engages the retention plug 620 to secure the second sterilizing panel 606 to the table top 602. The retention plug 608 may be disengages from the retention plug 622, and the retention plug 614 disengaged from the retention plug 620, by operation of the associated release mechanism 116.

With this embodiment, a table top 602 of a sterilizing instrument table 600 may be substantially larger than a size that would fit in an autoclave, but each sterilizing panel may be independently removed and autoclaved after use.

In some embodiments, the retention plug(s) 608, 614, 620, and 622 may comprise one or more spring-loaded elements, notched elements, bayonet elements, bayonet fixators and/or locking parts.

In some embodiments, the retention plug(s) 608, 614, 620, and 622 may comprise different but correspondingly shaped elements configured to interact to removably attach to one another. For example, retention plug 608 may be configured to interact with retention plug 622 and may comprise a different by interacting shape and/or configuration. Similarly, retention plug 614 may be configured to interact with retention plug 622 and may comprise a different by interacting shape and/or configuration.

As an example, one retention plug may comprise a notched bayonet while the corresponding retention plug may comprise a receiving attachment. The notched bayonet may enter the receiving attachment and with spring loaded pressure set its notch on a small shelf or catchment in the receiving attachment. The receiving attachment may be sized to be large enough to allow translating the bayonet away from the edge, clearing it for removal. As an example, a tapered end of the bayonet may allow for lowering one element over another before the bayonet clicks in place. In some embodiments, to allow for spring loaded attachment the sterilizing instrument table 600 may also comprise a simple receiving smooth port sized exactly to receive a smooth, non-notched bayonet to fix the two notched bayonets against the receiving edges of the receiving attachment.

Figure 7:
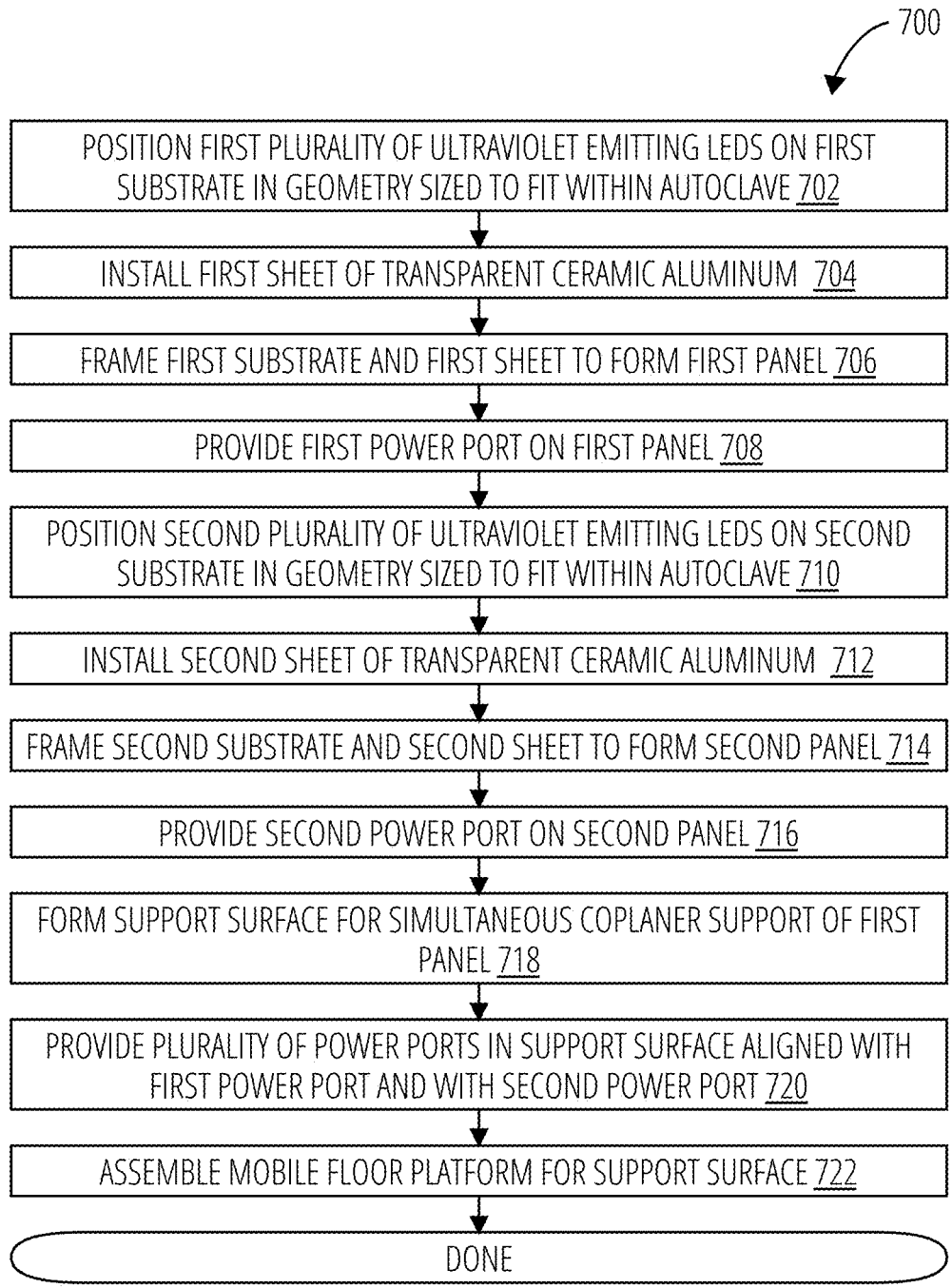
FIG. 7 illustrates an assembly process 700 in accordance with one embodiment.

An embodiment of the sterilizing instrument table 600 may be constructed according to the assembly process 700 of FIG. 7.

Referring to FIG. 7, in block 702, a first plurality of ultraviolet LEDs are positioned on a first substrate in a geometry sized to fit within an autoclave. In block 704, a first sheet of transparent ceramic aluminum (or other UV transparent sterilizable material) is installed in thermal contact with at least a portion of the first LEDs. In block 706, the first substrate and first sheet are framed to form a first panel. In block 708, a first power port is provided on the first panel. In block 710, a second plurality of ultraviolet LEDs are positioned on a second substrate in a geometry sized to fit within the autoclave. In block 712, a second sheet of transparent ceramic aluminum (or other UV transparent sterilizable material) is installed in thermal contact with at least a portion of the second LEDs. In block 714, the second substrate and second sheet are framed to form a second panel. In block 716, a second power port is provided on the second panel. In block 718, a support surface is formed for simultaneous co-planer support of the first panel and the second panel. In block 720, a plurality of power ports are provided in the support surface, aligned with the first power port and with the second power port. In block 722, a mobile floor platform is assembled for the support surface.

It may be advantageous to adjust the intensity of the LED light emitted from the panels in proportion to detected air flow. This may save energy and incident exposure to UV radiation during times of low air flow, and may improve sterilization when the air is moving quickly. Thus the sterilization may be applied not only the instruments resting on the panel, but to the volume of air exposed to the LED light.

Figure 8:
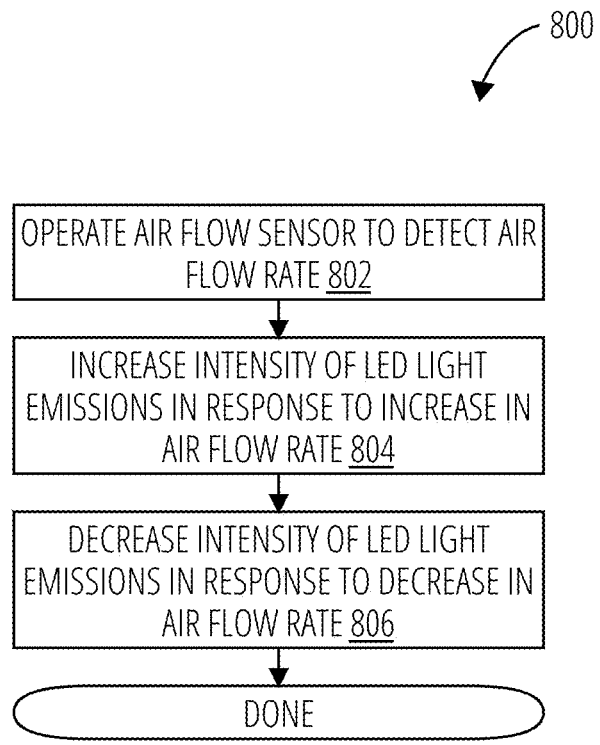
FIG. 8 illustrates an LED control process 800 in accordance with one embodiment.

FIG. 8 illustrates an LED control process 800 in accordance with one embodiment.

In block 802, an air flow sensor is operated to detect an air flow rate. In block 804, an intensity of LED light is increased in response to an increase in the air flow rate or air agitation (or to ambient sound, which is proportional to air flow rate or agitation). In block 806, an intensity of LED light emissions is decreased in response to a decrease in the air flow rate and/or agitation.

Figure 9:
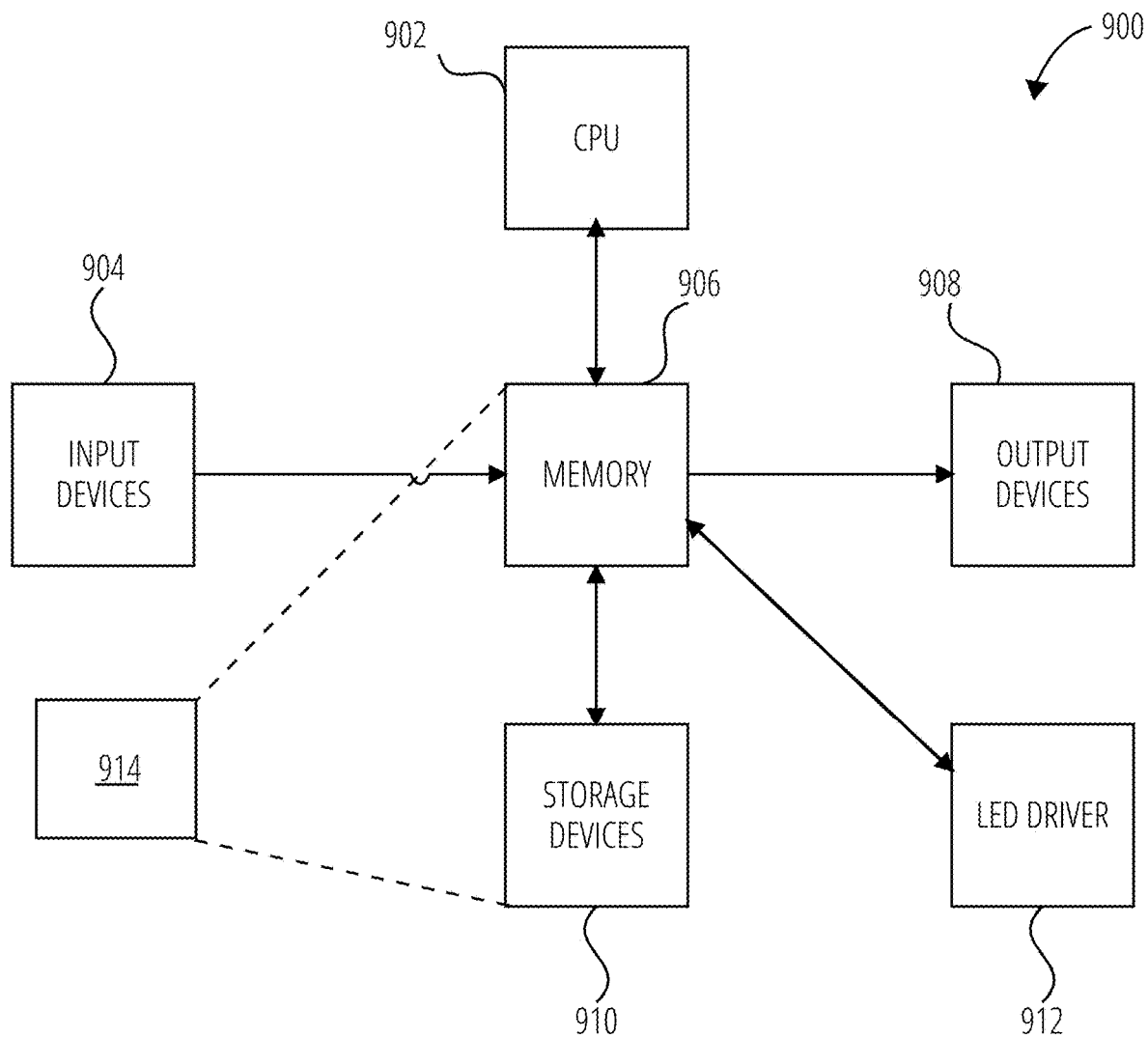
FIG. 9 illustrates an embodiment of a controller 900 to operate the sterilizing panel systems described herein.

FIG. 9 illustrates an embodiment of a controller 900 to operate the sterilizing panel systems described herein.

Input devices 904 comprise transducers that convert physical phenomenon into machine internal signals, typically electrical, optical or magnetic signals. Signals may also be wireless in the form of electromagnetic radiation in the radio frequency (RF) range but also potentially in the infrared or optical range. Examples of input devices 904 are buttons or keys which respond to touch or physical pressure from an object or proximity of an object to a surface, touch screens which respond to motion through space or across a plane, temperature sensors, and air pressure, sound, or air motion sensors. The signals from the input devices 904 are provided via various machine signal conductors (e.g., busses or network interfaces) and circuits to memory 906.

The memory 906 is typically what is known as a first or second level memory device, providing for storage (via configuration of matter or states of matter) of signals received from the input devices 904, instructions and data for controlling operation of the CPU 902, and signals from storage devices 910.

The memory 906 and/or the storage devices 910 may store computer-executable instructions and thus forming logic 914 that when applied to and executed by the CPU 902 implement embodiments of the processes disclosed herein.

Information stored in the memory 906 is typically directly accessible to the CPU 902 of the device. Signals input to the device cause the reconfiguration of the internal material/energy state of the memory 906, creating in essence a new machine configuration, influencing the behavior of the controller 900 by affecting the behavior of the CPU 902 with control signals (instructions) and data provided in conjunction with the control signals.

Second or third level storage devices 910 may provide a slower but higher capacity machine memory capability. Examples of storage devices 910 are hard disks, optical disks, large capacity flash memories or other non-volatile memory technologies, and magnetic memories.

The CPU 902 may cause the configuration of the memory 906 to be altered by signals in storage devices 910. In other words, the CPU 902 may cause data and instructions to be read from storage devices 910 in the memory 906 from which may then influence the operations of CPU 902 as instructions and data signals, and from which it may also be provided to the output devices 908. The CPU 902 may alter the content of the memory 906 by signaling to a machine interface of memory 906 to alter the internal configuration, and then converted signals to the storage devices 910 to alter its material internal configuration. In other words, data and instructions may be backed up from memory 906, which is often volatile, to storage devices 910, which are often non-volatile.

Output devices 908 are transducers which convert signals received from the memory 906 into physical phenomenon such as vibrations in the air, or patterns of light on a machine display, or vibrations (i.e., haptic devices) or patterns of ink or other materials (i.e., printers and 3-D printers).

The LED driver 912 receives signals from the memory 906 or the CPU 902 and converts them into electrical signals to the LEDs of the panels. The led driver 912 may also communicate signals to the memory 906 or the CPU 902.

Having described various devices and methods herein, exemplary embodiments or aspects can include, but are not limited to:

In a first embodiment, an apparatus may comprise a first plurality of ultraviolet light emitting diodes (UV LEDs) positioned in a first substrate; a first sheet of transparent material in thermal contact with at least a portion of the first plurality of ultraviolet light emitting diodes; a first frame surrounding the first substrate and the first sheet, forming a first panel; and a mobile platform to support the first panel over a floor, the mobile platform adapted to receive the first panel in a configuration such that light emitted from the first plurality of ultraviolet light emitting diodes is directed in an upward direction from the floor.

A second embodiment can include the apparatus of the first embodiment, wherein the transparent material is transparent ceramic aluminum.

A third embodiment can include the apparatus of the first or second embodiments, the mobile platform comprising a release mechanism to engage and disengage the first panel.

A fourth embodiment can include the apparatus of any of the first through third embodiments, wherein the first panel has a rectangular shape.

A fifth embodiment can include the apparatus of any of the first through fourth embodiments, further comprising a second plurality of ultraviolet LEDs positioned on a second substrate; a second sheet of transparent material in thermal contact with the second ultraviolet LEDs; and a second frame surrounding the second substrate and the second sheet, forming a second panel; the mobile platform comprising a two-tiered bracket configured to receive the first panel and the second panel in a configuration such that the first sheet and the second sheet are aligned with and facing one another.

A sixth embodiment can include the apparatus of the fifth embodiment, wherein the mobile platform comprises a release mechanism to engage and disengage the first panel.

A seventh embodiment can include the apparatus of any of the fifth or sixth embodiment, further comprising the first panel comprising a first panel power port; the second panel comprising a second panel power port; and the mobile platform comprising a first platform power port and a second platform power port to respectively engage the first panel power port and second panel power port automatically when the first panel and second panel are placed on the mobile platform.

An eighth embodiment can include the apparatus of any of the first through seventh embodiments, further comprising a second plurality of ultraviolet LEDs positioned on a second substrate; a second sheet of transparent material in thermal contact with the second ultraviolet LEDs; a second frame surrounding the second substrate and the second sheet, forming a second panel; the first panel comprising a first panel power port; the second panel comprising a second panel power port; and the mobile platform comprising a first platform power port and a second platform power port to respectively engage the first panel power port and second panel power port automatically when the first panel and second panel are placed on the mobile platform.

A ninth embodiment can include the apparatus of the eighth embodiment, the mobile platform comprising a release mechanism to engage and disengage the first panel and the second panel.

A tenth embodiment can include the apparatus of any of the first through ninth embodiments, wherein the first substrate comprises a geometry sized to fit within an autoclave.

In an eleventh embodiment, an assembly method may comprise positioning a first plurality of ultraviolet LEDs on a first substrate; fixing a first sheet of transparent material in thermal contact with the first ultraviolet LEDs; forming a first frame surrounding the first substrate and the first sheet, forming a first panel; and assembling a mobile platform to support the first panel over a floor, the mobile platform adapted to receive the first panel in a configuration such that light emitted from the first ultraviolet LEDs is directed in an upward direction from the floor.

A twelfth embodiment can include the method of the eleventh embodiment, wherein the transparent material is transparent ceramic aluminum.

A thirteenth embodiment can include the method of the eleventh or twelfth embodiments, the mobile platform comprising a release mechanism to engage and disengage the first panel.

A fourteenth embodiment can include the method of any of the eleventh through thirteenth embodiments, wherein the first panel has a rectangular shape.

A fifteenth embodiment can include the method of any of the eleventh through fourteenth embodiments, further comprising positioning a second plurality of ultraviolet LEDs on a second substrate; fixing a second sheet of transparent material in thermal contact with the second ultraviolet LEDs; forming a second frame surrounding the second substrate and the second sheet, forming a second panel; and equipping the mobile platform with a two-tiered bracket configured to receive the first panel and the second panel in a configuration such that the first sheet and the second sheet are aligned with and facing one another.

A sixteenth embodiment can include the method of the fifteenth embodiment, further comprising equipping the mobile platform with a release mechanism to engage and disengage the first panel.

A seventeenth embodiment can include the method of the fifteenth or sixteenth embodiment, further comprising providing the first panel with a first panel power port; providing the second panel with a second panel power port; and equipping the mobile platform with a first platform power port and a second platform power port to respectively engage the first panel power port and second panel power port automatically when the first panel and second panel are placed on the mobile platform.

An eighteenth embodiment can include the method of any of the eleventh through seventeenth embodiments, further comprising positioning a second plurality of ultraviolet LEDs on a second substrate; fixing a second sheet of transparent material in thermal contact with the second ultraviolet LEDs; forming a second frame surrounding the second substrate and the second sheet, forming a second panel; equipping the first panel with a first panel power port; equipping the second panel with a second panel power port; and equipping the mobile platform with a first platform power port and a second platform power port to respectively engage the first panel power port and second panel power port automatically when the first panel and second panel are placed on the mobile platform.

A nineteenth embodiment can include the method of the eighteenth embodiment, further comprising equipping the mobile platform with a release mechanism to engage and disengage the first panel and the second panel.

A twentieth embodiment can include the method of any of the eleventh through nineteenth embodiments, further comprising sizing the first substrate with a geometry to fit within an autoclave.

Terms used herein should be accorded their ordinary meaning in the relevant arts, or the meaning indicated by their use in context, but if an express definition is provided, that meaning controls.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Programmable device" in this context refers to an integrated circuit designed to be configured and/or reconfigured after manufacturing. The term "programmable processor" is another name for a programmable device herein. Programmable devices may include programmable processors, such as field programmable gate arrays (FPGAs), configurable hardware logic (CHL), and/or any other type programmable devices. Configuration of the programmable device is generally specified using a computer code or data such as a hardware description language (HDL), such as for example Verilog, VHDL, or the like. A programmable device may include an array of programmable logic blocks and a hierarchy of reconfigurable interconnects that allow the programmable logic blocks to be coupled to each other according to the descriptions in the HDL code. Each of the programmable logic blocks may be configured to perform complex combinational functions, or merely simple logic gates, such as AND, and XOR logic blocks. In most FPGAs, logic blocks also include memory elements, which may be simple latches, flip-flops, hereinafter also referred to as "flops," or more complex blocks of memory. Depending on the length of the interconnections between different logic blocks, signals may arrive at input terminals of the logic blocks at different times.

"Software" in this context refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

Those skilled in the art will recognize that it is common within the art to describe devices or processes in the fashion set forth herein, and thereafter use standard engineering practices to integrate such described devices or processes into larger systems. At least a portion of the devices or processes described herein can be integrated into a network processing system via a reasonable amount of experimentation. Various embodiments are described herein and presented by way of example and not limitation.

Those having skill in the art will appreciate that there are various logic implementations by which processes and/or systems described herein can be effected (e.g., hardware, software, or firmware), and that the preferred vehicle will vary with the context in which the processes are deployed. If an implementer determines that speed and accuracy are paramount, the implementer may opt for a hardware or firmware implementation; alternatively, if flexibility is paramount, the implementer may opt for a solely software implementation; or, yet again alternatively, the implementer may opt for some combination of hardware, software, or firmware. Hence, there are numerous possible implementations by which the processes described herein may be effected, none of which is inherently superior to the other in that any vehicle to be utilized is a choice dependent upon the context in which the implementation will be deployed and the specific concerns (e.g., speed, flexibility, or predictability) of the implementer, any of which may vary. Those skilled in the art will recognize that optical aspects of implementations may involve optically-oriented hardware, software, and or firmware.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein. The techniques and procedures described herein may be implemented via logic distributed in one or more computing devices. The particular distribution and choice of logic will vary according to implementation.

The foregoing detailed description has set forth various embodiments of the devices or processes via the use of block diagrams, flowcharts, or examples. Insofar as such block diagrams, flowcharts, or examples contain one or more functions or operations, it will be understood as notorious by those within the art that each function or operation within such block diagrams, flowcharts, or examples can be implemented, individually or collectively, by a wide range of hardware, software, firmware, or virtually any combination thereof. Portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more processing devices (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

In a general sense, those skilled in the art will recognize that the various aspects described herein which can be implemented, individually or collectively, by a wide range of hardware, software, firmware, or any combination thereof can be viewed as being composed of various types of circuitry.

What is claimed is:

1. An apparatus comprising:
a first plurality of ultraviolet light emitting diodes positioned in a first substrate;
a first sheet of transparent material in thermal contact with at least a portion of the first plurality of ultraviolet light emitting diodes;
a first frame surrounding the first substrate and the first sheet, forming a first panel; and
a mobile platform to support the first panel over a floor, the mobile platform adapted to receive the first panel in a configuration such that light emitted from the first plurality of ultraviolet light emitting diodes is directed in an upward direction from the floor;
a second plurality of ultraviolet light emitting diodes positioned on a second substrate; a second sheet of transparent material in thermal contact with at least a portion of the second plurality of ultraviolet light emitting diodes;
a second frame surrounding the second substrate and the second sheet, forming a second panel; and the mobile platform comprising a two-tiered bracket configured to receive the first panel and the second panel in a configuration such that the first sheet and the second sheet are aligned with and facing one another;
the first panel comprising a first panel power port;
the second panel comprising a second panel power port; and
the mobile platform comprising a first platform power port and a second platform power port to respectively engage the first panel power port and second panel power port automatically when the first panel and second panel are placed on the mobile platform.

2. An apparatus comprising:
a first plurality of ultraviolet light emitting diodes positioned in a first substrate;
a first sheet of transparent material in thermal contact with at least a portion of the first plurality of ultraviolet light emitting diodes;
a first frame surrounding the first substrate and the first sheet, forming a first panel; and
a mobile platform to support the first panel over a floor, the mobile platform adapted to receive the first panel in a configuration such that light emitted from the first plurality of ultraviolet light emitting diodes is directed in an upward direction from the floor;
a second plurality of ultraviolet light emitting diodes positioned on a second substrate;
a second sheet of transparent material in thermal contact with the second plurality of ultraviolet light emitting diodes;
a second frame surrounding the second substrate and the second sheet, forming a second panel;
the first panel comprising a first panel power port;
the second panel comprising a second panel power port; and
the mobile platform comprising a first platform power port and a second platform power port to respectively engage the first panel power port and second panel power port automatically when the first panel and second panel are placed on the mobile platform.

3. The apparatus of claim 2, the mobile platform comprising a release mechanism to engage and disengage the first panel and the second panel.

4. An assembly method, comprising:
positioning a first plurality of ultraviolet light emitting diodes on a first substrate;
fixing a first sheet of transparent material in thermal contact with at least a portion of the first plurality of ultraviolet light emitting diodes;
forming a first frame surrounding the first substrate and the first sheet, forming a first panel;
assembling a mobile platform to support the first panel over a floor, the mobile platform adapted to receive the first panel in a configuration such that light emitted from the first plurality of ultraviolet light emitting diodes is directed in an upward direction from the floor;
positioning a second plurality of ultraviolet light emitting diodes on a second substrate;
fixing a second sheet of transparent material in thermal contact with at least a portion of the second plurality of ultraviolet light emitting diodes;
forming a second frame surrounding the second substrate and the second sheet, forming a second panel;
equipping the mobile platform with a two-tiered bracket configured to receive the first panel and the second panel in a configuration such that the first sheet and the second sheet are aligned with and facing one another;
providing the first panel with a first panel power port; providing the second panel with a second panel power port; and
equipping the mobile platform with a first platform power port and a second platform power port to respectively engage the first panel power port and second panel power port automatically when the first panel and second panel are placed on the mobile platform.

5. An assembly method, comprising:
positioning a first plurality of ultraviolet light emitting diodes on a first substrate;
fixing a first sheet of transparent material in thermal contact with at least a portion of the first plurality of ultraviolet light emitting diodes;
forming a first frame surrounding the first substrate and the first sheet, forming a first panel;
assembling a mobile platform to support the first panel over a floor, the mobile platform adapted to receive the first panel in a configuration such that light emitted from the first plurality of ultraviolet light emitting diodes is directed in an upward direction from the floor;
positioning a second plurality of ultraviolet light emitting diodes on a second substrate; fixing a second sheet of transparent material in thermal contact with at least a portion of the second plurality of ultraviolet light emitting diodes;
forming a second frame surrounding the second substrate and the second sheet, forming a second panel; equipping the first panel with a first panel power port;
equipping the second panel with a second panel power port; and
equipping the mobile platform with a first platform power port and a second platform power port to respectively engage the first panel power port and second panel power port automatically when the first panel and second panel are placed on the mobile platform.

6. The method of claim 5, further comprising equipping the mobile platform with a release mechanism to engage and disengage the first panel and the second panel.

* * * * *